United States Patent [19]
Fukui et al.

[11] 3,966,822
[45] June 29, 1976

[54] CATALYTIC PREPARATION OF KETONES FROM ALDEHYDES

[75] Inventors: Masahiro Fukui; Shigeru Hayashi; Takehiko Okamoto; Isao Koga; Takeshi Inoi, all of Yokohama, Japan

[73] Assignee: Chisso Corporation, Osaka, Japan

[22] Filed: Apr. 27, 1972

[21] Appl. No.: 248,133

[30] Foreign Application Priority Data
May 19, 1971 Japan................................ 46-33774
Jan. 19, 1972 Japan................................ 47-7438

[52] U.S. Cl. .................... 260/593 R; 260/586 C; 260/590 L; 260/591; 260/592
[51] Int. Cl.² ........................................ C07C 45/00
[58] Field of Search ......... 260/586 R, 586 B, 593 R

[56] References Cited
UNITED STATES PATENTS

| | | |
|---|---|---|
| 3,248,428 | 4/1966 | Porter et al. ..................... 260/593 R |
| 3,316,303 | 4/1967 | Mertzweiller et al. ............. 60/593 R |
| 3,384,668 | 5/1968 | Canter et al. ....................... 260/593 |
| 3,542,878 | 11/1970 | Swift ............................ 260/593 R X |
| 3,666,816 | 5/1972 | Tagaki et al. ..................... 260/593 R |

Primary Examiner—Norman Morgenstern
Attorney, Agent, or Firm—Fred Philpitt

[57] ABSTRACT

Symmetrical and unsymmetrical ketones are produced from aldehydes (aliphatic, alicyclic or aromatic aldehydes) or their mixtures according to the process of the present invention which comprises contacting the aldehydes or mixtures theirof with a catalyst selected from the group consisting of zirconium oxide and combinations of zirconium oxide with an alkali metal oxide and/or an alkaline earth metal oxide. Said catalyst is used with or without a carrier. The process is operated in the vapor phase at elevated temperature in the presence or absence of steam.

5 Claims, No Drawings

CATALYTIC PREPARATION OF KETONES FROM ALDEHYDES

DESCRIPTION OF THE INVENTION

This invention relates to a process for preparing ketones from aldehydes using a novel catalyst. More particularly, this invention is concerned with a process for preparing from aldehydes, the corresponding ketones by allowing aldehydes or their mixtures to come in contact with a catalyst selected from the group consisting of zirconium oxide and combinations of zirconium oxide with an alkali metal oxide and/or alkaline earth metal oxide, which is used with or without supporting carrier such as activated carbon, pumice, activated alumina, silica-alumina, silica-gel, clay, kiesel-guhr, celite, etc.

Heretofore, several processes have been proposed to prepare from two molecules of aldehydes, one molecule of the corresponding ketones. For example, a method for preparing acetone from acetaldehyde using zinc oxide or calcium oxide as a catalyst is well known. Further, it is known that a chromium oxide catalyst is useful for preparing a ketone from a lower aliphatic linear aldehyde, but its conversion is at most 28%, and furthermore, in the case of branched aldehydes, olefins are mainly formed, and particularly in the case of aldehydes having a substituent at the α-position, for example, isobutyraldehyde, no reaction takes place at all.

Recently, the conversion of isobutyraldehyde to diisopropyl ketone through contact with lithium oxide carried on alumina has been proposed [U.S. Pat. No. 3,410,909 (1968)]. Further, it has been disclosed that aldehydes, especially isobutyraldehyde, can be converted to diisopropyl ketone by a catalyst containing an oxidized form of a rare earth metal having an atomic number from 59 to 71, or lithium, thorium, or lanthanum carried on alumina [U.S. Pat. No. 3,453,331 (1969); French Pat. No. 1,524,596 (1968)].

However, these processes have the following disadvantages: the conversion or selectivity is relatively low; an amount of ketone formed per unit weight of the catalyst is so low that the efficiency is not attractive; fatty acids are produced as corrosive by-products; and the cost of catalyst is relatively expensive.

As a result of strenuous study and research of a process for preparing from aldehydes the corresponding ketones, the present inventors have found that zirconium oxide is a very suitable novel catalyst as it is or when supported on carriers, and that zirconium oxide is favorably activated by an addition of one or more alkali metal oxides and/or alkaline earth metal oxides, and have accomplished the present invention on the basis of said finding.

When the present catalysts are used, an aldehyde is converted to the corresponding ketone in a high yield in the presence or absence of steam at a relatively high temperature; the rate of ketone formation is increased; the amount of ketone produced per unit time and unit amount of catalyst is increased; and the amount of by-products such as fatty acids is quite small.

This means that higher space-time-yield can be obtained by the use of the present catalysts as compared with the known catalysts mentioned above.

Moreover, the present catalysts have a long life, and even if deactivated by coking, they can be readily reactivated to their initial state by introducing air through the reaction tube.

Particularly in the case of the combination catalysts of zirconium oxide with an alkali metal oxide and/or an alkaline earth metal oxide, the above-mentioned effectivenesses are remarkable.

Preparations of the catalysts used in the present invention will be illustrated as follows;

The zirconium oxide catalyst can be prepared by subjecting the nitrate, oxynitrate, sulfate, phosphate, oxychloride, hydroxide, organic acid salts, alkoxides, carbonates, basic carbonate, ammonium carbonate or the like of zirconium, to direct calcination, or by converting water-soluble salts among the above-mentioned salts of zirconium to hydroxide, using an alkaline substance such as aqueous ammonia solution, followed by filtering, drying and calcination. This case also includes preparation of mixtures of hydroxides by co-precipitation of these water-soluble salts with activated alumina sol or silica sol in the presence of an alkaline material.

The combination catalysts of zirconium oxide with alkali metal oxide and/or alkaline earth metal oxide can be prepared by mixing the above-mentioned water soluble salts of these metals in the same procedures as mentioned above. The combination catalysts can be also obtained by immersing zirconium oxide in an aqueous solution of water-soluble salts of alkali metal and/or alkaline earth metal followed by drying and calcination.

It is, forthermore, possible to obtain a catalyst supported on carriers by impregnating an aqueous solution of water-soluble salts of zirconium in a carrier such as activated carbon, pumice, activated alumina, silica-alumina, silica-gel, clay, kiesel-guhr, celite, etc. followed by drying and calcination. In this case, an aqueous solution of water-soluble salts of alkali metal and/or alkaline earth metal may be added to the solution of water-soluble salts of zirconium.

As to the amount of zirconium oxide of the combination catalysts, from 99.5% to 60% by weight is suitable, and from 99.5% to 90% is more preferable, the balance being alkali metal oxide and/or alkaline earth metal oxide.

A temperature of from 200°C to 1,000°C can be employed as the calcination temperature, and a temperature range of 300°C to 700°C is preferable.

The catalyst is pelletized into a proper size.

As for the aldehydes used in this process, there can be used linear or branched aliphatic aldehydes having 2–10 carbon atoms, alicyclic aldehydes having a general formula of $C_y$—RCHO (wherein $C_y$ is cyclohexyl or cyclohexenyl and R is 0 – 2 carbon atoms), aromatic aldehydes having a general formula of Ph-R'CHO (where Ph is phenyl and R' is an aliphatic carbon chain having 0 – 5 carbon atoms), and mixtures thereof.

As for concrete examples, there can be illustrated aliphatic aldehydes such as acetaldehyde, propionaldehyde, n-butyraldehyde, iso-butyraldehyde, valeraldehyde, caproic aldehyde, heptaldehyde, caprylaldehyde, 2-ethylhexylaldehyde, pelargonic aldehyde, capric aldehyde, etc.; alicyclic aldehydes such as cyclohexyl acetaldehyde, 3-cyclohexene-1-aldehyde, 6-methyl-3-cyclohexene-1-aldehyde, 3-cyclohexene-1-acetaldehyde, etc.; and aromatic aldehydes such as benzylaldehyde, 1-phenylpropionaldehyde, 2-phenylpropionaldehyde, etc.

Reaction conditions will be explained as follows:

The conversion of aldehydes into the desired ketones can be achieved within the temperature range from 200°C to 600°C, preferably from about 300°C to 500°C.

The reaction is readily effected at atmospheric pressure. However, super-atmospheric or subatmospheric pressure such as that of about 0.1 to 10 atmospheres can be also used satisfactorily.

It is preferable to feed aldehyde at a rate ranging from 0.1 to 30 g/hour/gram of the catalyst.

The present catalytic reaction is preferably carried out in the presence of water vapor although it is possible in the absence thereof.

The molar ratio of aldehyde in the feed ranging from zero to 100, preferably 0.1 to 5, can be employed. These two raw materials are fed to a reactor as vapor.

As for the ketones produced, there can be illustrated acetone, diethyl ketone, methyl ethyl ketone, methyl propyl ketone, methyl isopropyl ketone, diisopropyl ketone, di-n-propyl ketone, di-n-butyl ketone, di-n-pentyl ketone, di-n-hexyl-ketone, di-n-hetyl ketone, di(1-ethyl pentyl) ketone, di-n-octyl ketone, di-n-nonyl ketone, di-cyclohexyl ketone, bis(3-cyclohexenyl) ketone, bis(6-methyl-3-cyclohexenyl) ketone, bis(tetrahydrobenzyl) ketone, benzophenone, di-benzyl ketone, diphenenetyl ketone, bis($\alpha$-methylbenzyl) ketone, etc.

The ketones produced according to this invention are useful as solvents for rubbers, elastomers, polyvinyl acetate and other plastics. They are also useful as reaction solvents, extracting solvents, and intermediate compounds. The following examples are presented to illustrate the invention. In these examples, conversion and selectivity are given in mole-percent.

EXAMPLE 1

Zirconium hydroxide was heated at 300°C for an hour and successively at 700°C for 7 hours to give zirconium oxide. The zirconium oxide was pelletized into a 3×3mm cylindrical size. 15g of the thus obtained zirconium oxide as catalyst was packed in a quarts reaction tube having an inner diameter of 23mm and a length of 630mm. Definite amounts of acetaldehyde, water, and nitrogen (as a carrier), preheated at 350°C, were fed into the reactor at its one end. The reaction system was kept at 400°C. After passing through the reaction tube, the reactants were further passed through a condenser, whereby a liquid product was obtained. The amounts of the materials fed into the reaction tube were as follows:

| | |
|---|---|
| acetaldehyde; | 7.1 g/hour/gram of the catalyst |
| water; | 0.44 as a molar ratio of water/aldehyde |
| nitrogen; | 2.4 L/hour |

The conversion of acetaldehyde was 40%, and the selectivity of acetone was 95%.

EXAMPLE 2

Addition of an aqueous 25% ammonium hydroxide solution to an aqueous 20% zirconium oxynitrate solution gave a gelatinous material, which was aged overnight, filtered and dried at 110°C. Then it was calcined at 300°C for an hour and successively at 600°C for 3 hours. It was pelletized in the same manner as in example 1.

19g of the thus obtained catalyst was packed in the same reaction tube as in Example 1. Isobutyraldehyde was fed into the reactor at a rate of 1.9 g/hour/gram of the catalyst; water, at a molar ratio of water to aldehyde of 0.73; and nitrogen, at a rate of 2.4 L/hour, after these materials were preheated through a preheater at 350°C. The results of the experiments at various temperatures are shown in Table 1.

Table 1

| Test No. | Reaction temperature °C | Conversion % | Selectivity of DIPK* % | Mol ratio of water/aldehyde |
|---|---|---|---|---|
| a | 400 | 30.8 | 83.3 | 0.73 |
| b | 440 | 50.1 | 84.1 | 0.73 |
| c | 470 | 89.5 | 88.3 | 0.73 |
| d | 500 | 99.3 | 82.9 | 0.73 |
| e | 440 | 33.9 | 57.3 | 0 (no water) |

*DIPK = Diisopropyl ketone

Isobutyric acid was produced in a small quantity at elevated temperature.

EXAMPLE 3

Reaction was carried out using 15g of the same catalyst as in example 1, and acetaldehyde and isobutyraldehyde as raw materials, under the following conditions:

| | |
|---|---|
| acetaldehyde; | 2.1 g/hour/gram of the catalyst |
| isobutyraldehyde; | 4.9 g/hour/gram of the catalyst |
| water; | 0.8 as a molar ratio of water to each aldehyde, respectively |
| nitrogen; | 24 L/hour |
| reaction temperature; | 450°C |

Methyl isopropyl ketone, acetone and diisopropyl ketone were obtained as main products. The conversions were 66.2% based on acetaldehyde, and 50.2% based on isobutyraldehyde. The selectivities of methyl isopropyl ketone, acetone and diisopropyl ketone were 28.3%, 35.1%, and 25.8%, respectively.

EXAMPLE 4

To a mixture of aqueous solutions of aluminum and zirconium nitrates, aqueous 25% ammonium hydroxide solution was added to coprecipitate a mixture of hydroxides, followed by water-washing, filtering and drying at 100°C. Next, the resultant material was calcined at 300°C for 2 hours, and successively at 600°C for 3 hours. The ratio by weight of $Al_2O_3$ to $ZrO_2$ of the resulting catalyst was 20 : 80.

30g of the catalyst was packed in the same reactor as in Example 1, and isobutyraldehyde and water preheated at 350°C were fed thereto under the following reaction conditions:

| | |
|---|---|
| isobutyraldehyde; | 1.1 g/hour/gram of the catalyst |
| water; | 0.61 as a molar ratio of water/aldehyde |
| nitrogen; | 2.4 L/hour |
| reaction of temperature; | 440°C |

The conversion of isobutyraldehyde was 71.8%, and the selectivity of diisopropyl ketone was 83.5%.

EXAMPLE 5

Activated carbon was impregnated with an aqueous solution of zirconium nitrate so that the content of zirconium oxide might be 15% by weight based upon the total amount of the activated carbon and zirconium oxide, and then dried at about 90°C for 3 hours. Next, it was calcined at 300°C for 3 hours.

30g of thus obtained catalyst was packed in the same reactor as in Example 1, and heated at 500°C for 3 hours under nitrogen atmosphere. Isobutyraldehyde and water, preheated at 350°C, were fed to the reactor, under the following reaction conditions:

| | |
|---|---|
| isobutyraldehyde; | 4.2 g/hour/gram of the catalyst |
| water; | 1.01 as a molar ratio of water/aldehyde |
| nitrogen; | 2.4 L/hour |
| reaction temperature; | 450°C |

The conversion of isobutyraldehyde was 49.7% and the selectivity of diisopropyl ketone was 65.3%.

EXAMPLE 6

Reaction was carried out using 17g of the same catalyst as in Example 2, and 2-ethylhexylaldehyde as a raw material, under the following reaction conditions:

| | |
|---|---|
| 2-ethylhexylaldehyde; | 3.4 g/hour/gram of the catalyst |
| water; | 0.55 as a molar ratio of water/aldehyde |
| nitrogen; | 2.4 L/hour |
| reaction temperature; | 395°C |

The conversion of aldehyde was 35.1% and the selectivity of di(1-ethylpentyl) ketone was 85.3%.

EXAMPLE 7

Reaction was carried out using 25g of the same catalyst as in Example 4, and acetaldehyde and benzaldehyde as raw materials, under the following reaction conditions:

| | |
|---|---|
| acetaldehyde; | 3.7 g/hour/gram of the catalyst |
| benzaldehyde; | 9.0 g/hour/gram of the catalyst |
| water; | 0.61 as a molar ratio of water to each aldehyde, respectively |
| nitrogen; | 2.4 L/hour |
| reaction temperature; | 420°C |

Main product were methyl phenyl ketone, acetone and benzophenone. The conversions of acetaldehyde and benzaldehyde were 44.5% and 41.7%, respectively. The selectivities of methyl phenyl ketone, acetone and benzophenone were 25.8%, 35.3% and 21.7%, respectively.

Example 8

Reaction was carried out in the same manner as in Example 1, except that 20g of the catalyst was used, and 3-cyclohexene-1-aldehyde was fed to the reactor. The reaction conditions were as follows:

| | |
|---|---|
| 3-cyclohexene-1-aldehyde; | 3.0 g/hour/gram of the catalyst |
| water; | 0.5 as a molar ratio of water/aldehyde |
| nitrogen; | 2.4 L/hour |
| reaction temperature; | 450°C |

The conversion of the aldehyde was 85%, and the selectivity of bis(3-cyclohexenyl) ketone was 80%.

EXAMPLE 9

Various catalysts were prepared using zirconium oxychloride as a starting material.

Catalyst No. 2 was prepared by adding and dissolving an aqueous solution of magnesium nitrate to a 27% aqueous solution of zirconium oxychloride so that the molar ratio of $MgO/ZrO_2$ might be 0.02, and adding concentrated ammonia solution to the resulting solution mixture to precipitate a hydroxide mixture. The mixture was treated as in Example 2, and 3×3mm pelletized was obtained.

Catalyst No. 3 was similarly prepared except that zirconium oxychloride, magnesium nitrate and potassium nitrate were used as starting materials, so that the molar ratio of $ZrO_2 : MgO : K_2O$ might be 94.2 : 4.0 : 1.8.

Catalyst No. 4 was similarly prepared from zirconium oxychloride and calcium hydroxide.

These catalyst were calcined at 300°C for an hour and successively at 600°C for 3 hours.

Isobutyraldehyde was used as a raw material, and reactions were carried out in the same manner as in Example 2, under the following reaction conditions:

| | |
|---|---|
| amount of catalyst; | 19g |
| isobutyraldehyde; | 1.9 g/hour/gram of the catalyst |
| water; | 0.73 as a molar ratio of water/aldehyde |
| reaction temperature; | 440°C |

The results are shown in Table 2. For comparison's sake, the result obtained by the use of the same catalyst as in Example 2 is also described in the Table, as Catalyst No. 1.

Table 2

| Catalyst No. | 1 | 2 | 3 | 4 |
|---|---|---|---|---|
| Composition of catalyst (%) | $ZrO_2$ 100 | $ZrO_2$ 98<br>MgO 2 | $ZrO_2$ 94.2<br>$K_2O$ 1.8<br>MgO 4.0 | $ZrO_2$ 65<br>CaO 35 |
| Conversion of isobutyraldehyde (%) | 50.1 | 92.1 | 87.1 | 60.1 |
| Selectivity of DIPK* (%) | 84.1 | 92.3 | 91.0 | 87.7 |

*diisopropyl ketone

As shown in Table 2, catalysts consisting of zirconium oxide and alkali metal oxide and/or alkaline earth metal oxide were improved to increase the reaction rate as compared with that of zirconium oxide alone.

Example 10

Catalyst No. 2 and No. 3 were prepared using magnesium nitrate or potassium nitrate in a similar manner to Example 9. These catalyst were calcined at 300°C for an hour and successively at 600°C for 3 hours. Isobutyraldehyde was used as a raw material. The reactions were carried out as in Example 2, and the reaction conditions were as follows:

| | |
|---|---|
| amount of catalyst; | 19g |
| isobutyraldehyde; | 1.9 g/hour/gram of the catalyst |
| water; | 0.73 as a molar ratio of water/aldehyde |
| reaction temperature | 440°C |

The results of the experiment are shown in Table 3. For comparison's sake, the result by the use of the same catalyst as in Example 2 is also described in Table 3, as catalyst No. 1.

Table 3

| Catalyst No. | | 1 | 2 | 3 |
|---|---|---|---|---|
| Composition of catalyst (%) | | ZrO$_2$ 100 | ZrO$_2$ 98 MgO 2 | ZrO$_2$ 98 K$_2$O 2 |
| Initial state | Conversion (%) | 52.6 | 90.9 | 88.4 |
| | Selectivity of DIPK (%) | 84.3 | 92.4 | 90.5 |
| After 1000 hours operation | Conversion (%) | 39.1 | 88.1 | 89.9 |
| | Selectivity of DIPK (%) | 78.5 | 92.5 | 91.3 |

The table shows that the catalysts consisting of ZrO$_2$ and MgO or K$_2$O have a longer catalyst life than that of ZrO$_2$ alone.

It is clear that alkali metal oxide and alkaline earth metal oxide have a remarkable effect in suppressing the coking of catalyst which leads to the deactivation of the catalyst.

What is claimed is:

1. A decarboxylation process which consists essentially of contacting two mols of an aldehyde of the formula R$_1$CHO or one mol of an aldehyde of the formula R$_1$CHO and one mol of the formula R$_2$CHO wherein R$_1$ and R$_2$ are different alkyl groups, in the vapor phase and in the presence of water with a catalyst in an amount effective to produce a ketone of the formula R$_1$COR$_1$ or R$_1$COR$_2$ said aldehydes R$_1$CHO and R$_2$CHO being selected from the group consisting of acetaldehyde, propionaldehyde, N-butyraldehyde, isobutyraldehyde, valeraldehyde, caproic aldehyde, heptaldehyde, caproylaldehyde, 2-ethylhexyl aldehyde, pelargonic aldehyde, capric aldehyde and mixtures thereof, said catalyst being selected from the group consisting of:
 a. 100% zirconium oxide
 b. Zirconium oxide and an alkali metal oxide, and
 c. zirconium oxide and an alkaline earth metal oxide,
said elevated temperature being within the range of 200° – 600°C.

2. The process of claim 1 wherein the feed rate of aldehyde is from 0.1 to 30 g/hour/gram of catalyst.

3. The process of claim 1 wherein the temperature is from about 300°C to about 500°C.

4. The process of claim 1 wherein the mole ratio of water to aldehyde in the feed is between 0.1 to 5.

5. A decarboxylation process which consists essentially of contacting two mols of an aldehyde of the formula R$_1$CHO or one mol of an aldehyde of the formula R$_1$CHO and one mol of the formula R$_2$CHO, wherein R$_1$ and R$_2$ are different alkyl groups, in the vapor phase and in the presence of water with a catalyst in an amount effective to produce a ketone of the formula R$_1$COR$_1$ or R$_1$COR$_2$ said aldehydes R$_1$CHO and R$_2$CHO being selected from the group consisting of acetaldehyde, propionaldehyde, N-butyraldehyde, isobutryaldehyde, valeraldehyde, caproic aldehyde, heptaldehyde, caproylaldehyde, 2-ethylhexyl aldehyde, pelargonic aldehyde, capric aldehyde and mixtures thereof, said catalyst being selected from the group consisting of
 a. from 99.5% to 60% by weight of zirconium oxide and from 40% to 0.5% by weight of alkali metal oxide and
 b. 99.5% to 60% by weight of zirconium oxide and 0.5 – 40% by weight of an alkaline earth metal oxide said elevated temperature being within the range of 200° – 600°C.

* * * * *